(12) United States Patent
Martel

(10) Patent No.: US 8,353,624 B2
(45) Date of Patent: Jan. 15, 2013

(54) TEST DEVICE FOR CHECKING A PRE-VACUUM STEAM STERILIZATION APPARATUS

(75) Inventor: Paul Martel, St. Raphael (FR)

(73) Assignee: Sterlab, Vallauris (FR)

( * ) Notice: Subject to any disclaimer, the term of this patent is extended or adjusted under 35 U.S.C. 154(b) by 78 days.

(21) Appl. No.: 12/895,972

(22) Filed: Oct. 1, 2010

(65) Prior Publication Data

US 2011/0243181 A1    Oct. 6, 2011

(30) Foreign Application Priority Data

Oct. 2, 2009  (FR) ...................................... 09 56895

(51) Int. Cl.
*G01N 25/60*    (2006.01)

(52) U.S. Cl. .......................................... 374/42

(58) Field of Classification Search ...................... 374/42
See application file for complete search history.

(56) References Cited

U.S. PATENT DOCUMENTS

| | | | |
|---|---|---|---|
| 4,486,387 A | 12/1984 | Augurt | |
| 4,579,715 A | 4/1986 | Bruso | |
| 5,066,464 A | 11/1991 | Augurt | |
| 5,422,276 A * | 6/1995 | Colvin | 436/1 |
| 5,491,092 A * | 2/1996 | Colvin | 436/1 |
| 5,989,852 A * | 11/1999 | Hendricks et al. | 435/31 |
| 6,630,352 B1 | 10/2003 | Reiner et al. | |

FOREIGN PATENT DOCUMENTS

| | | | |
|---|---|---|---|
| EP | 0776669 A1 | 6/1997 | |
| FR | 2892309 A1 | 4/2007 | |
| WO | 9321964 A1 | 11/1993 | |
| WO | WO 9321964 A1 * | 11/1993 | |
| WO | 9532742 A1 | 12/1995 | |
| WO | WO 9532742 A1 * | 12/1995 | |
| WO | 9712637 A1 | 4/1997 | |
| WO | WO 9712637 A1 * | 4/1997 | |

* cited by examiner

*Primary Examiner* — Lisa Caputo
*Assistant Examiner* — Jamel Williams
(74) *Attorney, Agent, or Firm* — Bachman & LaPointe, P.C.

(57) ABSTRACT

Test device capable of checking the quality of the sterilizing steam in a pre-vacuum apparatus intended for sterilization, including a receptacle forming an elongate chamber closed at its distal end and open at its proximal end, in which the chamber contains a filling load, and at least one undesirable gas presence indicator arranged toward the distal closed end of the chamber. According to the invention; the undesirable gas presence indicator is an electronic temperature sensor, and the filling load comprises at least, in the operating position, one path enabling a flow by gravity of the water condensed in the chamber from the steam primarily forming the atmosphere of same, to the opening of the proximal end.

12 Claims, 4 Drawing Sheets

TEST DEVICE FOR CHECKING A PRE-VACUUM STEAM STERILIZATION APPARATUS

BACKGROUND

This invention relates to a test device for checking a pre-vacuum steam sterilization apparatus.

The technical field of the invention is that of the production of test devices capable of checking the quality of the sterilizing gas such as steam in a pre-vacuum apparatus intended for sterilization with said steam, and in which it is therefore desirable to determine the efficacy of the vacuum produced before introducing said steam, and then the quality of the latter once introduced into the chamber.

This invention is intended in particular for tests of pre-vacuum and steam sterilization apparatuses such as, but not exclusively, autoclaves used to sterilize medical and hospital equipment.

The so-called BOWIE-DICK test method has been known since 1961 and has been the subject of various publications, and it is therefore unnecessary to explain it in this application: reference can be made to various prior patent applications that refer to this method, such as application U.S. Pat. No. 4,579,715 published on Apr. 1, 1986 by the WARNER LAMBERT Company or U.S. Pat. No. 4,486,387 published on Dec. 4, 1984 by the PROPPER MANUFACTURING Company or even that of the MXM Company filed on Oct. 20, 2005 and published under number FR 2 892 309, on which this introduction is largely based.

It will simply be noted that the objective of this test is to verify that there is no longer any undesirable gas, in this case non-condensable, in the chamber of the sterilizing apparatus: for this, an ink sensitive to the sterilization gas is generally used, such as a chemical composition sensitive to moisture, but not to the undesirable gases, and placed according to various patterns on a measurement sheet slid inside a pack of porous material or in a hollow receptacle closed at one end and open at the other; said receptacle or pack is placed in the sterilization apparatus during a test cycle that is performed, up to 134° C., at a predetermined frequency, before said apparatus is used to sterilize equipment. Such a test, of which the result is therefore verified after being removed from the apparatus, thus makes it possible to ascertain that there were no more undesirable gases such as air in the chamber, because these gases could become stratified, create pockets of which the temperature could not be controlled, or become mixed with the sterilizing gas, thereby adversely affecting the quality of the sterilization: if the test is positive, i.e. the sensitive ink changed color over the entire surface of the pattern, it can be deduced that there were no undesirable gases during the test cycle and that the same will be true during subsequent equipment sterilization phases.

Various patent applications have been filed to protect various aspects of test devices, including those cited above and, also, among those with a receptacle in the family to which the present invention belongs:

U.S. Pat. No. 6,630,352, published on Jul. 1, 1999 by the 3M INNOVATIVE PROPERTIES COMPANY, which describes and claims a complex device with a vertical receptacle of which the opening faces downward and is surrounded by an external radiator for removing the heat contained in the chamber of the receptacle, which is free of any load and which includes two temperature sensors located against and outside it so as to measure the temperature at two points on the wall;

U.S. Pat. No. 5,066,464, published on Nov. 19, 1991 by the PROPPER MANUFACTURING COMPANY, INC, which describes and claims a device also including a receptacle but arranged horizontally, in which the cross-section of the opening is larger than that of the closed end, in which the chamber of said receptacle includes a heat dissipater formed by a large non-woven "field" sheet "stuffed" by hand into said chamber in order to condense the vapor, and a chemical indicator that is sensitive to moisture such as by changing color, and arranged toward the closed end of the chamber of the receptacle.

These two examples of embodiments describe the same principle of air/steam separation by progression and condensation along a receptacle with heat dissipation devices in order to condense the steam and thus concentrate undesirable gases such as air, which are in the form of radiators placed outside the chamber or in the form of filling loads placed inside, and with a measuring device that is either electronic and placed outside or that is chemical and placed inside.

The problem stated and not completely solved by any of the documents known from the prior art is that of obtaining results that are reliable and as satisfactory as possible, that of not having to use a test pack that must be opened after use, as in the solution of the patent of the MXM Company, FR 2 892 309 cited above, and, finally, that of simplifying the test devices with a receptacle such as that of U.S. Pat. No. 6,630,352 of the 3M INNOVATIVE PROPERTIES COMPANY, cited above, even if the electronic sensor solution is easier to use than the chemical devices such as that of the U.S. Pat. No. 5,066,464 of the PROPPER MANUFACTURING COMPANY INC, of which the chemical indicator must be removed in order to verify the state afterward, and of which the results are associated with the operator's interpretation of the colorimetric change.

SUMMARY OF THE INVENTION

A solution to the stated problem is a test device capable of checking for the presence of non-condensable undesirable gases, and therefore the quality of the sterilizing steam in a pre-vacuum apparatus intended for sterilization of objects with said steam, and including an envelope holding elements of the device, including a receptacle forming an elongate chamber closed at its distal end and open at its proximal end, in which said chamber contains a filling load occupying at least a portion of its volume, and at least one indicator of the presence of undesirable gases arranged toward the distal closed end of the chamber. According to the invention:

the envelope has a high thermal inertia at least around the distal end of the chamber where the undesirable gas presence indicator is arranged, the undesirable gas presence indicator is an electronic temperature sensor of any type, which is capable of enabling the proportion of said non-condensable undesirable gas in the atmosphere at the distal end of the chamber to be calculated, the filling load is such that it comprises at least, in the operating position of the chamber of the receptacle containing it, one path enabling a flow by gravity of the water condensed in the chamber of the receptacle from the steam primarily forming the atmosphere of same, to the opening of the proximal end.

In a preferred embodiment, the filling load consists of one or at least one rigid element, and preferably more than one separate elements, preferably having a regular external geometric shape such as a sphere, in which said separate elements can be balls of rigid material, such as steel, glass, and so on.

It is also preferable for the surface of the wall of the receptacle forming the elongate chamber to be a surface of revolution of which the generatrix arranged at the very bottom of the operating device forms and angle α between 0 and 90°, and preferably between 0 and 30°, or even between 0 and 10°, with respect to and below the horizontal, from the closed base of the receptacle to the proximal open end.

In another preferred embodiment, the receptacle is a cylinder of which the axis AA' forms, in operation, an angle α between 0 and 90° with respect to the horizontal, in which the center of the opening is at least at the same level or below that of the distal closed end.

The result is a new type of test device responding to the stated problem and the various disadvantages of the current devices since, on the one hand, we thus have a fairly simple test device, with an electronic measurement preventing the need to change (or even replace) the entire interior of the receptacle on each handling and also having much improved measurement results which have been quite surprisingly observed in trials.

It is noted that, before reaching thermal equilibrium, the temperature of a mixture of steam and undesirable gases such as air is below the temperature of the steam alone: by thus measuring the temperature in the atmosphere of the distal end inside the chamber of the receptacle according to the invention, if it is different from the temperature of the steam filling the atmosphere outside the device of the invention, there must be a concentration of undesirable gases and the latter are clearly present in the pre-vacuum sterilization apparatus to be tested; the greater the temperature difference is, the higher the proportion of non-condensable gases in the steam is (as may happen if the pre-vacuum failed, or if there was a supply of steam laden with such gases, or if there was a leakage, etc.).

Thus, in trials, of which the results are provided below, the aforementioned difference in temperature was measured in various configurations of the test device, each according to two situations, respecting the test conditions defined by ISO standard 11140-4, one in the absence of air (zero failure condition) and the other after air injections (characterizing failures: the criterion for good operation of the test device is thus to identify a near-zero temperature difference in the first situation and a large on in the second situation, and in any way in this case with a significant deviation (i.e. more than 15° C.) between the two differences so as to eliminate the risks of "background noise".

Four series of trials were thus carried out:

Trials 1: prior art with different chamber dimensions, in the form of a cylinder of revolution, without an internal load, as in the U.S. Pat. No. 6,630,352 cited above, and placed horizontally; however, with inadequate diameters, as shown by the first trial of these trials 1 with a diameter of 10 mm for a chamber length of 100 mm, the temperature difference, even in the absence of air, is much greater (67° C. in this example) and the comparison with a deviation in the presence of air cannot have any meaning; thus, the small diameters of 10 and 12 mm are eliminated, and only the diameter of 14 mm with a length of 70 mm is kept (the greater lengths producing temperature deviations, even in the presence of air, that are non-negligible are also to be eliminated: see trials 2 with, on the one hand, a length of mm and a diameter of 14 mm, and, on the other hand, a length of 70 mm and a diameter of 14 mm);

Trials 2: trials with rigid loads (very similar result with glass balls with a diameter of 3 mm, plastic granules, steel balls) in two chambers with different lengths, in the form of a cylinder of revolution, placed horizontally;

Trials 3: trials with rigid loads and the optimal chamber of trials 2, according to different tilts with respect to the horizontal.

A fourth series of trials with flexible loads produced better results than in the first series of trials, but with a wide dispersion of measurements which we have not reproduced in the table below (referenced FIG. 9).

FIG. 9

| | Tilt | L (mm) | Ø (mm) | Δ2Temp in absence of air | Δ2Temp in presence of air | Deviation | Conclusion |
|---|---|---|---|---|---|---|---|
| Trials 1 | 0° | 100 | 10 | 67.4 | X | X | Poor detection even in the absence of air: this small diameter is eliminated |
| | 0° | 80 | 12 | 23.7 | 29.7 | 6 | Insufficient detection |
| | 0° | 70 | 14 | 3.2 | 10.8 | 7.6 | Insufficient detection |
| Trials 2 | 0° | 80 | 14 | 13.7 | 35.4 | 21.7 | Acceptable |
| | 0° | 70 | 14 | 4.1 | 32.2 | 28.1 | Acceptable |
| | −90° | 70 | 14 | 2.1 | 17.1 | 15 | Limit |
| Trials 3 (average of 3 tests) | −10° | 70 | 14 | 1.0 | 22.9 | 21.9 | Acceptable |
| | 0° | 70 | 14 | 2.5 | 25.5 | 23 | Acceptable |
| | +2° | 70 | 14 | 38 | 41.9 | 3.9 | Poor detection |

These results were very surprising because they surpassed expectations in the choice of the configurations: they thus unexpectedly showed the importance, in order to have temperature deviations considered to be acceptable, of:

the tilt of the chamber of the receptacle, while the prior art discloses vertical and horizontal devices or without any suggestion of the need to control this tilt, even though, when a self-standing device is positioned on a support, it may cause a tilt according to its own configuration, and the presence of a load (having preferred features as indicated below) in the chamber, even though the prior art discloses devices without a load or with a flexible interior load, but without it being possible for a person skilled in the art to determine whether it plays an essential role and, even more, in association with the tilt; indeed, the trials have clearly demonstrated that a downward tilt of the opening of the receptacle with a load only very slightly influences the quality of detection of air, which remains excellent, whereas, by contrast, an upward tilt, even minor, capable of being caused by improper positioning of the device on its support (which must thus be specified, in the present invention, for the users, if the chamber of the device is horizontal by construction; and in order to limit such a risk of improper positioning, it may be preferable, as described below, to have a chamber of which the lower wall is tilted downward by construction, even if the device is intended normally to be positioned horizontally) produces situations in which the capacity to distinguish the presence from the absence of air is eliminated.

An essential feature according to the invention is therefore clearly that said load and the position, or the shape, of the receptacle containing it, must enable a flow by gravity of the water condensed in the chamber to the opening of same, and, according to a preferred embodiment, the load consists of a rigid element, or preferably a plurality of separate rigid elements, such as glass, plastic or steel balls.

BRIEF DESCRIPTION OF THE DRAWINGS

The appended figures show examples of embodiments of various devices according to the invention, but they are non-limiting.

DETAILED DESCRIPTION OF THE PREFERRED EMBODIMENT(S)

In all of the embodiments as shown here and other possible embodiments having the features of the invention, the device according to the invention includes a receptacle $1_1$ forming an elongate chamber 5 closed at its distal end 11 and open at its proximal end $1_2$, and said chamber 5 contains a filling load 3 occupying at least some of its volume. In the examples of embodiments shown in the appended figures, the ends $1_1$ and $1_2$ are arranged directly opposite one another in the same direction, but, in other embodiments, the receptacle may be curved and its ends, even if they may still be considered to be opposite one another with respect to the volume of the chamber 5, which is not straight and which separates them, would no longer be directly opposite one another (they may, for example, be in the same plane, as in the case in which the chamber is U-shaped).

Figure 1:
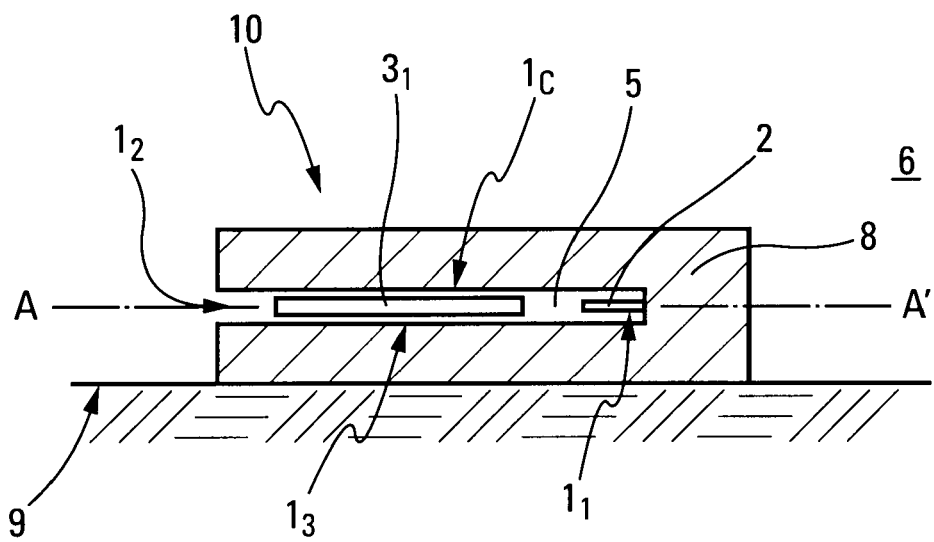
FIG. 1 shows a device according to the invention, which is free-standing and of which the envelope 8 is placed horizontally on a horizontal support 9, such as the lower wall of the chamber of the pre-vacuum steam sterilization apparatus to be tested: this device includes a cylindrical bore or receptacle having a horizontal axis, with a rigid load and a sensor arranged inside the base of said receptacle.
Figure 2:
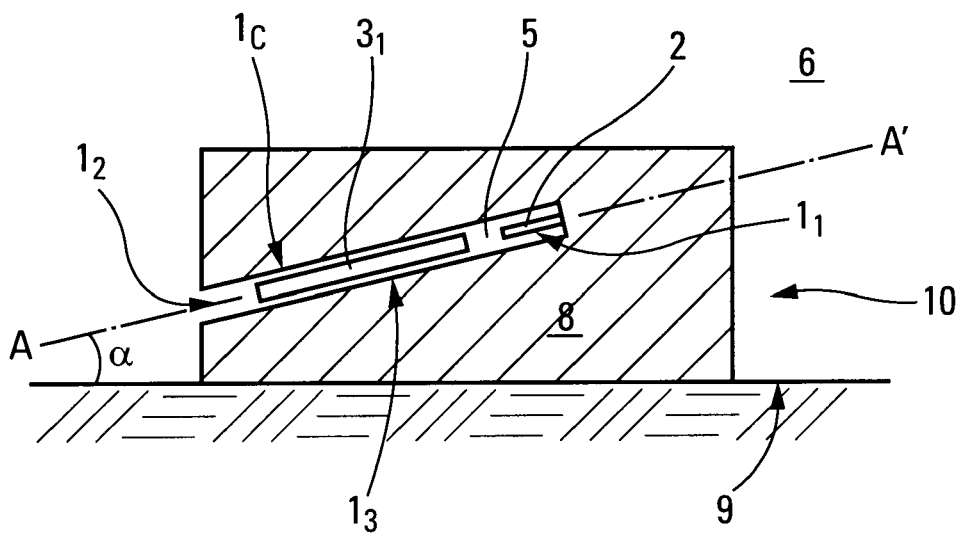
FIG. 2 is a device including the same features as in FIG. 1, but in which the axis of the chamber is clearly tilted, with the opening downward, even if the device is itself arranged horizontally.
Figure 3:
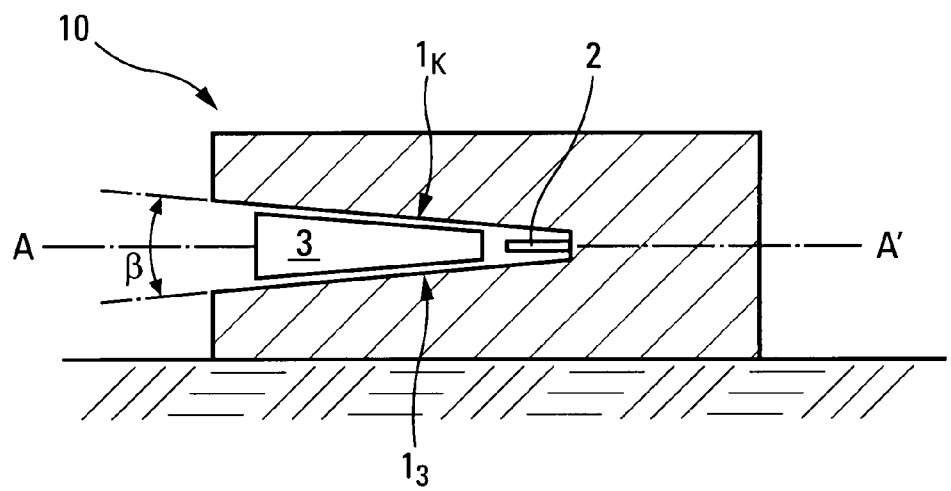
FIG. 3 is a device according to the invention arranged as in FIGS. 1 and 2, but in which the bore has a conical shape.
Figure 4:
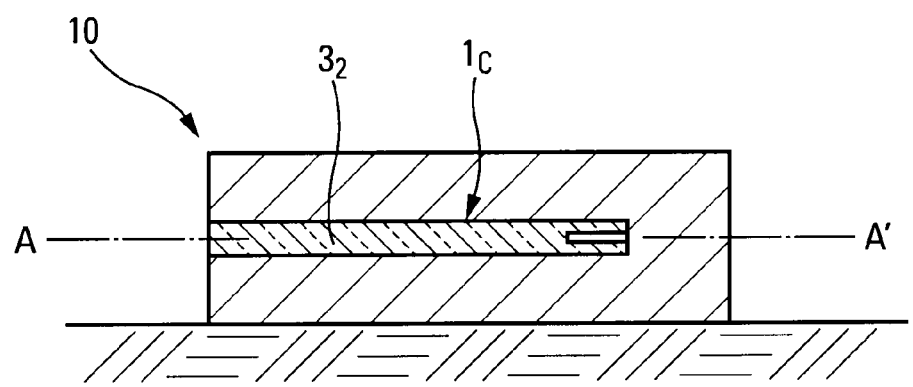
FIG. 4 is a device according to the invention of the type of FIG. 1, but with a porous rigid load.
Figure 5:
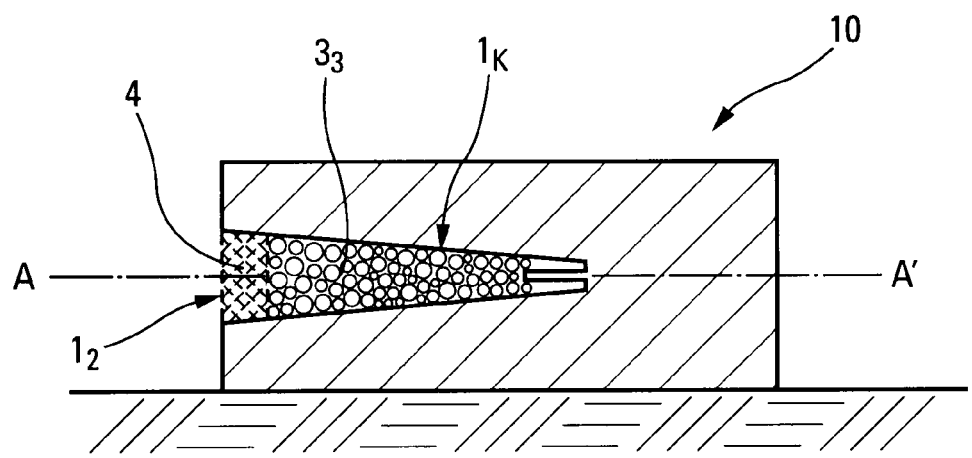
FIG. 5 is a device according to the invention of the type of FIG. 3, with a rigid load consisting of separate elements.
Figure 6:
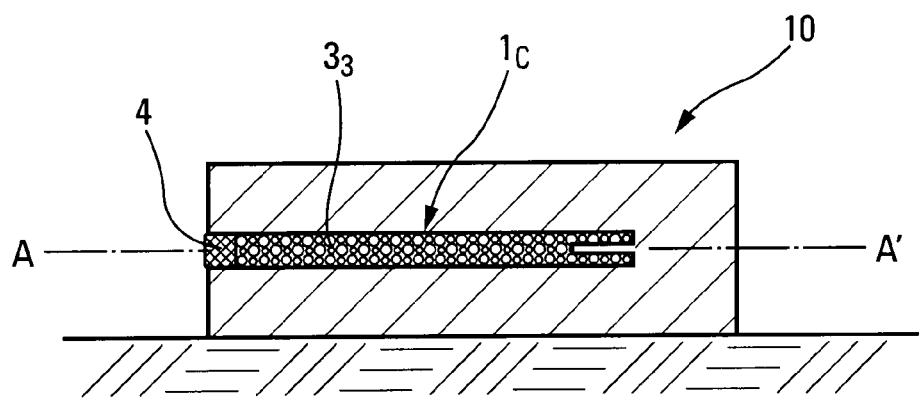
FIG. 6 is a device according to the invention of the type of FIG. 1, in which the rigid load consists of separate elements.
Figure 7:
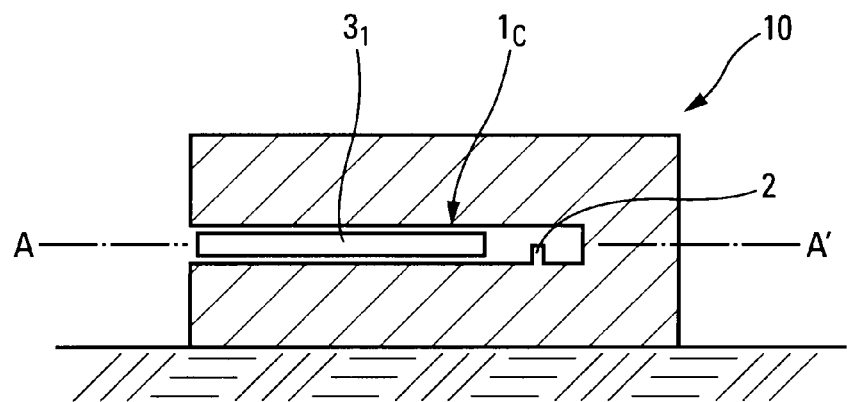
FIG. 7 is a device according to the invention of the type of FIG. 1, with a temperature sensor (indicator of the presence of undesirable gases, such as air) arranged inside and on the side wall of the receptacle.
Figure 8:
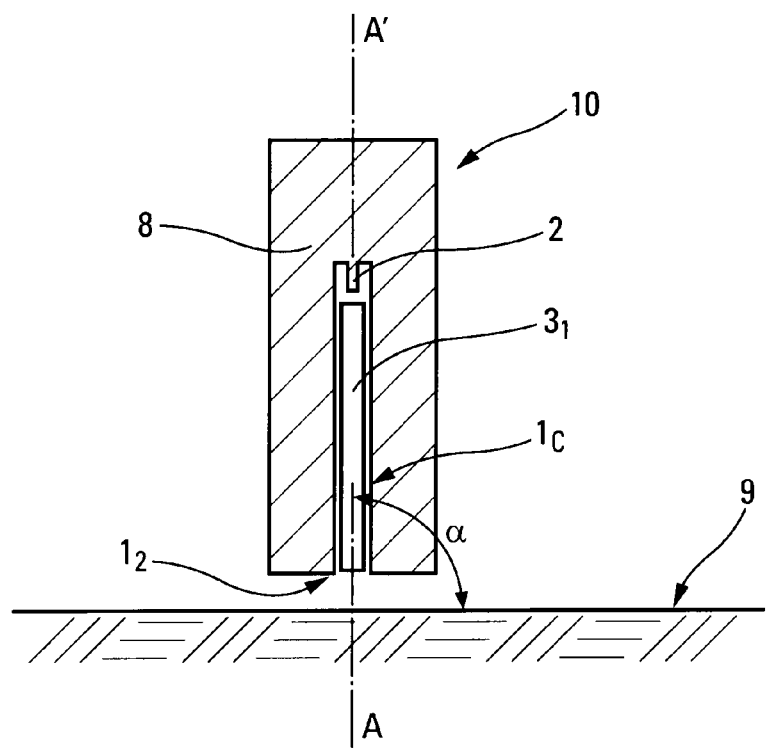
FIG. 8 shows a device according to the invention of the type of FIG. 1, but in which the envelope 8 is arranged with a maximum tilt of 90° with respect to the horizontal of the support 9, with the opening of the chamber directed downward.

The filling load 3 is such that it comprises at least, in the operating position of the chamber 5, one path enabling a flow by gravity of the water condensed in the chamber 5 from the steam primarily forming the atmosphere of same, to the opening of the proximal end $1_2$. This feature is obtained in all of the appended examples by the combination of two criteria:

the operating position of the chamber 5 must be such that the lower wall $1_3$ of the side wall of the bore or receptacle 1, arranged in operation at the very bottom of the device, is always at least horizontal (according to the example of FIGS. 1, 4, 6 and 7) or tilted from the base $1_1$ of the receptacle to its opening $1_2$, (as in FIG. 2 by the tilt of the axis A,A' of the bore or receptacle 1, if it is a cylinder $1c$, in particular of revolution, or by the choice of a bore in the shape of a cone $1k$ with a vertex angle β and in which, in operation, none of its generatrices forms an angle at the top with the horizontal, greater than β, as shown in FIGS. 3 and 5, or by tilting the entire device according to an angle α capable of reaching up to 90° with respect to the horizontal, in which the opening $1_2$ of the bore is directed downward, as in FIG. 8), the choice of the filling load, which can preferably be a rigid load such as an element made of a one-piece material $3_1$ non-porous to steam and to undesirable gases such as air, and which partially closes every section of the bore or receptacle 1, as in the representation of FIGS. 1 to 3, 7 and 8, but also a one-piece element $3_2$ formed by a material that is preferably rigid, porous to steam and to undesirable gases such as air and capable of completely occupying the section of the bore, as shown in FIG. 4, or, in a preferred embodiment, a plurality of separate elements $3_3$ capable of completely filling the section of the bore 1, as cited above in the trials (such as steel or glass balls, preferably with a diameter of 2 to 3 mm, or polypropylene granules such as those used to produce injection products) as shown in the examples of FIGS. 5 and 6; in this case, a buffer consisting of foam or another porous material, allowing all of the undesirable gases and steam to pass, but of course not the separate elements $3_3$, closes the proximal end $1_2$ of the chamber 5.

In the trials, as described above, it has been noted that the metal or steel balls are separate elements capable of forming the filling load and provide the greatest regularity in the assessment of the steam penetration, but these balls cause an increase in thermal inertia, which may be limiting. However, plastic balls or granules, by contrast, have a very low thermal inertia and react well to the detection of air; moreover, they are inexpensive, but further tests have nevertheless demonstrated that they have an unstable character over the long term. Consequently, the preferred choice may be glass balls, as tests have confirmed that they provide the best compromise.

Thus, in combination with the position and the shape of the receptacle as described above with a filling load according to the features above, there is always a path enabling a flow by gravity of the water condensed in the chamber 5 to the opening of the proximal end $1_2$.

The test device according to the invention also includes an undesirable gas presence indicator 2, arranged toward the distal closed end $1_1$ of the chamber 5, and, which, according to the invention, is an electronic temperature sensor capable of enabling the proportion of said non-condensable undesirable gas such as air in the atmosphere of the proximal end $1_2$ of the chamber 5 to be calculated.

This electronic temperature sensor 2 is positioned either preferably inside the volume of the chamber 5 so as to be in direct contact with the atmosphere of same, or in the thickness of the envelope 8, but near the wall of the receptacle 1 so as to provide temperature values, admittedly capable of being substantially different from those of the interior temperature of the distal end $1_1$ of the chamber 5, but nevertheless enabling sufficient distinction and reliability of the temperature deviation measurement as defined above.

This temperature measurement makes it possible, as explained above, to determine whether the device according to the invention has or has not concentrated the undesirable gases and therefore to determine whether the chamber in which it has been placed as indeed been emptied of all undesirable gases such as air before being filled with steam: the temperature indicated by said sensor 1 is recorded in an electronic device including a memory 7 housed in the envelope 8 of the device.

The envelope 8 must have a high thermal inertia, which can be obtained by any configuration, as a person skilled in the art can design it (such as, for example, by producing a case made of a plastic material resistant to heat (i.e. up to 135° C.) material, with a length of the envelope equal to twice that of the receptacle and a high thickness of this envelope such as an external diameter between twice and four times the internal diameter of the receptacle, which it thus insulates from the outside): this high thermal inertial must concern at least the portion of the envelope surrounding the distal end $1_1$ of the chamber 5, the end where the temperature sensor 2 is located, so that it is not subject to the influence of the external temperature, and the heat must then be conducted according to this invention only by the proximal end of the receptacle.

The device according to the invention can either be free-standing, with the envelope 8 being an independent and mobile case as shown in the figures, or the device is integrated in the pre-vacuum apparatus, with the envelope 8 then being capable of being an element of the chamber of the apparatus.

Said memory records this temperature for the entire measurement cycle, and the calculation of the percentage of non-condensable gases takes into account one or more values of this temperature for one or two moments of said cycle; the measurement of the temperature indicated by the internal sensor 2 is compared either to that of the external temperature measured and recorded at the same time by a sensor arranged outside the chamber 5, or to a predetermined reference temperature: the comparison of the difference between the two temperatures makes it possible to evaluate the percentage of non-condensable gas such as air capable of being found in the chamber considered, as explained in the presentation of trials described above.

This temperature sensor can be arranged against the base $1_1$ of the chamber 5 inside the bore or receptacle 1, as shown in all of FIGS. 1 to 6 and 7, but may also be arranged against the side wall $1_3$ of the chamber 5, inside the receptacle 1 but still toward the distal end $1_1$ of same. It may also be arranged in the same areas of the chamber 5, but, as indicated above, in the thickness of the envelope 8 and close to the wall of the chamber 5.

It may be noted that the device according to the invention can be used to "trap" air during operational sterilization cycles, and therefore without necessarily needing to include a temperature sensor since it would neither be necessary nor useful in such a case to perform a test measurement of the quality of the sterilizing gas, as the objective is to improve only the sterilization in the case of poor operation caused by air in the chamber (which would optionally have been measured beforehand by a test, or simply by precaution): in such a use, the device comprises a large chamber (with dimensions greater than those described above, since, for this objective of "trapping" air, it is necessary to be capable of having a large volume in order to concentrate and hold as much air as possible); such a large chamber may have a diameter of 20 to 50 mm and a length of 100 to 150 mm, for example, with a thermal inertia and therefore significant insulation (but less than in the case of a test device, since, in this case, the influence of the external temperature is less critical and therefore requires less thermal inertia): a thickness of 10 to 20 mm for the insulating wall of the envelope may be sufficient. Such a device necessarily comprises a filling load, as described above according to the invention, occupying at least some of the volume of the chamber of the receptacle, which must be arranged according to the same conditions as described for the test device.

The invention claimed is:

1. Test device capable of checking for the presence of non-condensable undesirable gases, and therefore the quality of the sterilizing steam in a pre-vacuum apparatus intended for sterilization with said steam, and including an envelope holding elements of the device, said test device including a receptacle forming an elongate chamber closed at a distal end and open at a proximal end; said chamber containing a filling load occupying at least a portion of a volume of said chamber; at least one undesirable gas presence indicator arranged toward the distal closed end of the chamber; the envelope having a high thermal inertia at least around the distal end of the chamber; the undesirable gas presence indicator comprising an electronic temperature sensor which is able to allow calculation of a proportion of said non-condensable undesirable gas in the atmosphere at the distal end of the chamber; and the filling load comprising at least, in an operating position of the chamber, one path enabling a flow by gravity of water condensed in the chamber from the steam primarily forming the atmosphere of the chamber, to the opening of the proximal end, wherein the filling load consists of at least one rigid element.

2. Test device according to claim 1, wherein a surface of a wall of the receptacle forming the elongate chamber is a surface of revolution, of which a generatrix arranged at a very bottom of the operating device forms an angle α between 0 and 90° with respect to and below a horizontal, from a closed base of the receptacle to the proximal open end.

3. Test device according to claim 1, wherein the receptacle is a cylinder of which an axis AA' forms, in operation, an angle α between 0 and 90° with respect to a horizontal, in which a center of an opening is at least at the same level or below that of the distal closed end.

4. Test device according to claim 3, wherein the receptacle is a cylinder of revolution.

5. Test device according to claim 2, wherein the surface of revolution is that of a cone with a vertex angle β in which, in operation, none of its generatrices forms an angle at the top with the horizontal greater than β.

6. Test device according to claim 1, wherein the temperature sensor is arranged against the base of a chamber, inside the receptacle.

7. Test device according to claim 1, wherein the temperature sensor is arranged against a side wall of the chamber, inside the receptacle, toward the distal end of the receptacle.

8. Test device according to claim 1, wherein the filling load consists of a one-piece element made of a material porous to steam and to undesirable gases.

9. Test device according to claim 1, wherein the filling load consists of a rigid one-piece element made of a material that is non-porous to steam and to undesirable gases and partially closing off every section of the receptacle.

10. Test device according to claim 1, wherein the filling load consists of a plurality of separate elements.

11. Test device according to claim 10, wherein the separate elements are balls made of a rigid material.

12. Test device according to claim 1, wherein the device is capable of being integrated in the pre-vacuum apparatus.

* * * * *